US008652061B2

United States Patent
Yu et al.

(10) Patent No.: US 8,652,061 B2
(45) Date of Patent: Feb. 18, 2014

(54) NONINVASIVE CUTANEOUS BLOOD FLOW ASSESSMENT AS A RESPONSE PREDICTOR FOR VISIBLE LIGHT THERAPY ON SEGMENTAL VITILIGO

(75) Inventors: Hsin-Su Yu, Kaohsiung (TW); Cheng-Che Lan, Kaohsiung (TW); Wei-Tai Yu, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 221 days.

(21) Appl. No.: 13/214,340

(22) Filed: Aug. 22, 2011

(65) Prior Publication Data

US 2012/0215120 A1 Aug. 23, 2012

(30) Foreign Application Priority Data

Feb. 17, 2011 (TW) .............................. 100105244 A

(51) Int. Cl.
*A61B 5/02* (2006.01)
*A61B 5/00* (2006.01)

(52) U.S. Cl.
USPC ........................................................ 600/504

(58) Field of Classification Search
USPC ........................................................ 600/504
See application file for complete search history.

(56) References Cited

PUBLICATIONS

"Low-Energy Helium-Neon Laser Therapy Induces Repigmentation and Improves the Abnormalities of Cutaneous Microcirculation in Segmental-Type Vitiligo Lesions," Wu, et al., Kaohsiung J Med Sci. Apr. 2008;24(4):180-9 (Wu 2008).*
"Cutaneous Blood Flow and Adrenoceptor Response Increase in Segmental-Type Vitiligo Lesions," Wu et al., J Dermatol Sci. May 2000;23(1):53-62 (Wu 2000).*
"Guidelines for Measurement of Cutaneous Blood Flow by Laser Doppler Flowmetry. A Report From the Standardization Group of the European Society of Contact Dermatitis," Bircher et al, Contact Dermatitis. Feb. 1994;30(2):65-72 (Bircher 1994).*
Wei-Tai Yu et al., Noninvasive cutaneous blood flow assessment as a response predictor for visible light therapy on segmental vitiligo: A prospective pilot study, Nov. 12, 2010.

* cited by examiner

*Primary Examiner* — Michael Kahelin
*Assistant Examiner* — Mitchell Alter
(74) *Attorney, Agent, or Firm* — WPAT, P.C.; Anthony King

(57) ABSTRACT

Visible light is a treatment option for Segmental Vitiligo (SV), and visible light-induced repigmentation is associated normalization of sympathetic. Currently it is difficult to predict individual patient's response to visible light therapy. Therefore, the present invention uses the Laser Doppler Flowmeter to serve as a response predictor for visible light on treating SV. The present invention recruited 14 Segmental Vitiligo patients for evaluating clinical information. FirstLaser Doppler Flowmeter was used to evaluate the cutaneous blood flow of SV lesion and contralateral normal skin, and then treated them with visible light irradiate, cold-stress, rewarmed, and recorded the change of skin blood flow, finally the patients received regular visible light treatment for 3 months, and patients have a sign of repigmentation after the treatment.

7 Claims, 5 Drawing Sheets

NONINVASIVE CUTANEOUS BLOOD FLOW ASSESSMENT AS A RESPONSE PREDICTOR FOR VISIBLE LIGHT THERAPY ON SEGMENTAL VITILIGO

FIELD OF THE INVENTION

The invention relates to predict a response for visible light therapy on Segmental Vitiligo (SV) via a noninvasive method.

DESCRIPTION OF PRIOR ART

Vitiligo is a depigmentary disorder with that acquired melanocyte is destroyed. With different disease types and courses, the skin of patient could appear big or small spots, the attack rate is about 1-2% thereof. Although the majority of SV do not cause damage and other clinical symptoms for patient body, patients feel annoyed with pigment difference of the skin for appearance.

Vitiligo can be classified into two distinct types in clinical manifestation and physiological response: (1) segmental vitiligo; and (2) non-segmental vitiligo. The first type occurs is associated with sympathetic dysfunction and distributes over the dermatomal position or the quasi-dematomal position, which causes significant effects on cutaneous blood flow. The second type is associated with immunity dysfunction, which belongs to autoimmune disease. Previous study with Laser Doppler Flowmeter showed that SV skin is associated with sympathetic dysregulation. However the same feature was not observed on non-segmental vitiligo skin. More specifically, the cutaneous blood flow and the adrenoceptor response in the SV lesion were significantly higher as compared to their contralateral normal skin.

For curing Vitiligo patients, low-energy Helium-Neon laser or visible-light have been used widely. However SV patients have to spend a lot of time treating, but there is not a judgment standard to predict the therapy outcome prior to treatment. The present invention can serve as a non-invasive predictor of the response to the light therapy, and serve as a standard to evaluate SV treating time with visible-light in clinical.

SUMMARY OF THE INVENTION

The present invention relates to a device for evaluating treatment effect of visible light on therapy Segmental Vitiligo (SV), the device comprising:
(a) a laser device for irradiating an lesion area with a visible light;
(b) a cooling device for cooling the affected area with a cool-stress after an irradiation of the visible light; and
(c) a blood flow detection device for measuring a blood flow of the affected area after the cool-stress.

The present invention relates to an evaluating method for visible-light therapy Segmental Vitiligo (SV), comprising the following steps of
(a) evaluating a blood flow of an affected area and a normal skin after a cool-stress
(b) after irradiating a visible-light, cooling and evaluating the blood flow of the affected area; and
(c) after a visible-light treatment, evaluating to determine treatment time.

DETAILED DESCRIPTION OF THE INVENTION

Figure 1:
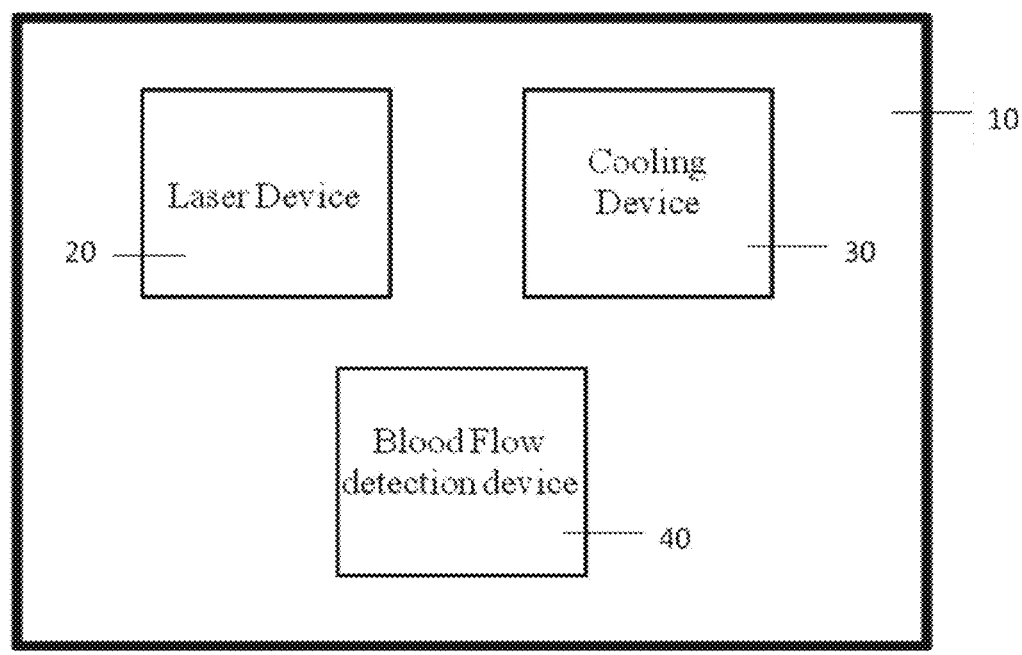
FIG. 1 is a device for evaluating SV treatment effect by visible-light.

In the past, Segmental Vitiligo patients have to spend a lot of time on the visible-light therapy, but the treatment outcome has not been predicted. Therefore, the present invention provides a device for evaluating the treatment effect for Segmental Vitiligo (SV) with light therapy (FIG. 1). In an embodiment, a device for evaluating Segmental Vitiligo (SV) treatment effect of a visible-therapy comprising a laser device for irradiating an affected area with a visible light, a cooling device for cooling the affected area with a cool-stress after an irradiation of the visible light, and a blood flow detection device for measuring a blood flow of the affected area after the cool-stress.

According to the device of the present invention for evaluating the effect of Segmental Vitiligo (SV) treatment of the visible-light therapy, the laser device emits a visible light of red light with a wavelength of 633±5 nm is preferred.

According to an embodiment of the present invention for evaluating Segmental Vitiligo treatment effect per the visible-light therapy, the preferred cooling device served to cool the affected area by the cool-stress after an irradiation of the visible light, wherein the temperature range is 0° C.~4° C. with which to determine the function of autonomic nerves.

According to an embodiment of the present invention for evaluating Segmental Vitiligo treatment effect per the visible-light therapy, the blood flow detection device is Laser Doppler flowmeter (PeriFlux System 5000, Perimed, Sweden), the blood flow in the capillary of SV affected area and control normal skin are measured by the blood flow detection device.

The present invention further provides an evaluating method for visible-light therapy for Segmental Vitiligo (SV), comprising the steps as following:
(a) evaluating a blood flow of an affected area and a normal skin after a cool-stress
(b) after irradiating a visible-light, cooling and evaluating the blood flow of the affected area; and
(c) after a visible-light treatment, clinically evaluating to determine treatment time.

In an embodiment, the affected area and normal skin were exposed to a cold-water packing at 0° C.~4° C. for 10 minutes per the cool-stress function of autonomic nerves of the patient skin was determined. In this stage, visible-light irradiation was not performed, In an embodiment, without irradiating by the visible light, the blood flow of the affected area (FIG. 3a) and the control skins (FIG. 3c) showed inconsistent changes (sporadic increase and decrease between two sequential recordings). After the first step was finished, the tested skins were remained equilibration for 30 minutes prior to the next stage. The second stage of pre-treatment evaluation, the affected skin of the Segmental Vitiligo patients receive a visible light irradiation and then place on the cold-water packing at 0° C.~4° C. for 10 minutes. After cooling the affected area, the blood flow is recorded by Doppler Flowmeter. In the preferred embodiment, after irradiated by a visible light, the blood flow variation of the affected area showed more consistent. In the third stage, patients received a continuous red visible-light with a wavelength of 633±5 nm three times per week, and for three months. The irradiating flux for each affected area is 3.0 J/cm² every time, and the power output is measured by a power meter (POW-105, Lasotronic).

In the present invention, the blood flow variation of the affected treated with the aforementioned steps (a) and (b) severed as a standard to predict the ongoing visible-light in clinical therapy. In a preferred embodiment, patients accept the visible light irradiation treatment before the blood flow variation is steady increase, and show a sign of repigmentation.

Thus, in the present invention, evaluation on blood flow of the skin after a visible-light irradiation can predict the response of the SV therapy.

EXAMPLE

Example 1

A Device for Evaluating Visible-Therapy Segmental Vitiligo (SV) Treatment Result The present invention provides a device (10) for evaluating the Segmental Vitiligo treatment effect by a visible-light therapy (e.g. FIG. 1). The device comprising a laser device (20), a cooling device (30) and a blood flow detection device (40). The laser device is used for irradiating the affected area with the visible light, and the wavelength range is 633±5 nm. The cooling device is used for cooling the affected area with the cool-stress at 0° C.~4° C. after visible light irradiation which determines a function of autonomic nerves of patients. The blood flow detection device is Doppler Flowmeter (PerFlux System 5000, Perimed, Sweden) is used for measuring the blood flow of the affected area after the cool-stress. Theoretically the blood flow is determined by the numbers of red blood cells moving in the measured volume as well as the average velocity. Analyzed by the analysis program kit (Perisoft, PeriFlux, PF3, Perimed), the data that stands for the mean values is displayed as Perfusion Unit (PU).

Example 2

An Evaluating Method for Visible-Therapy Segmental Vitiligo

Figure 2:
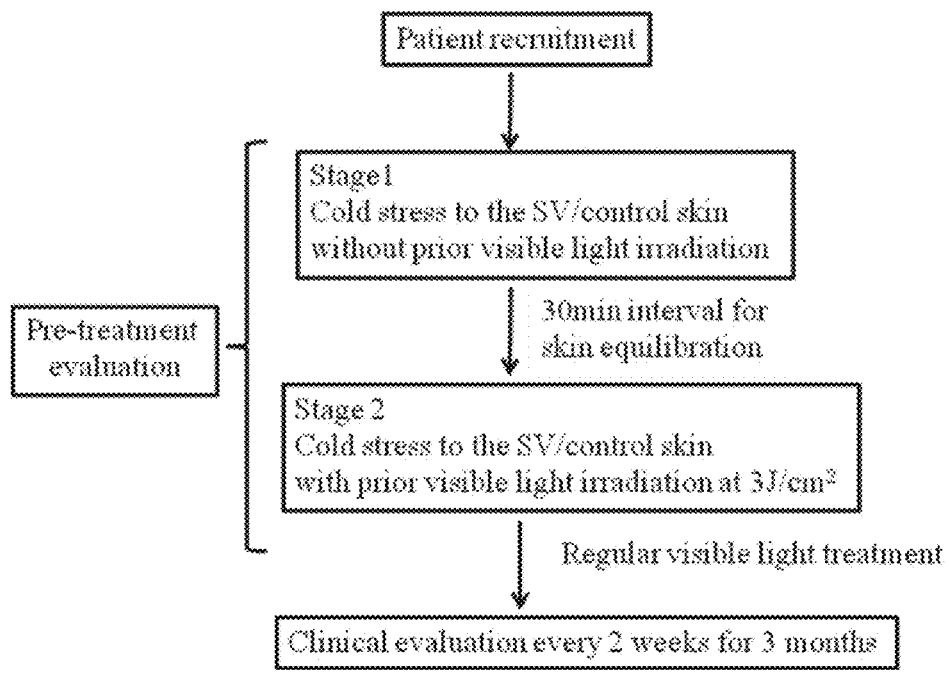
FIG. 2 is a schematic diagram of the evaluation processes for the SV treatment with light.

The present invention provides an evaluating method for visible-light therapy on Segmental Vitiligo (SV) (e.g. FIG. 2). The present invention first recruited 14 Segmental Vitiligo patients for evaluating clinical information (Table 1), and then provided a method for SV visible-light therapy comprising three steps.

(a) evaluating a blood flow of an affected area and a normal skin after a cool-stress
(b) after irradiating a visible-light, evaluating a blood flow of the affected area by the cool-stress; and
(c) after a visible-light treatment of clinically evaluating to determine treatment time.

Figure 3:
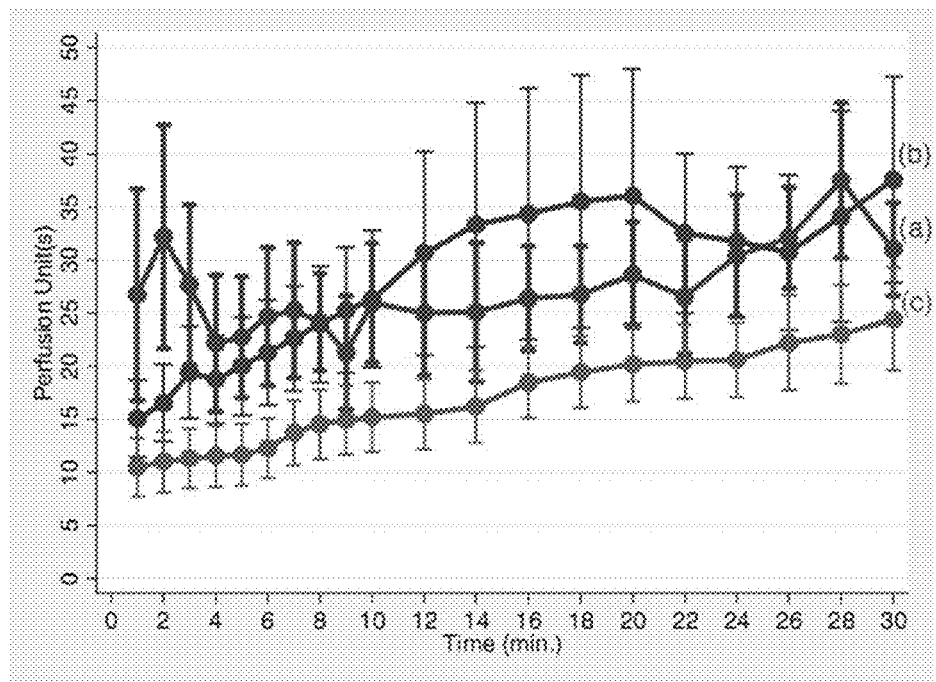
FIG. 3 is a perfusion-time chart for 50% SV patients through with/without prior visible light irradiation.

In the example, blood flow of the affected areas and the control skins were recorded and then placed in the cold-water packing at 0° C.~4° C. for 10 minutes. Via the cool-stress, function of autonomic nerves of the patient skin was determined. In this step, visible-light irradiation was not performed. Subsequently, the blood flow was recorded by Doppler Flowmeter. FIG. 3a and FIG. 3c show the affected area and the control skins without irradiating by the visible light, the blood flow of the affected area skins show inconsistent changes (sporadic increase and decrease between two sequential recordings). After the first step was finished, the tested skins were remained equilibration for 30 minutes before the next step continued.

Figure 4:
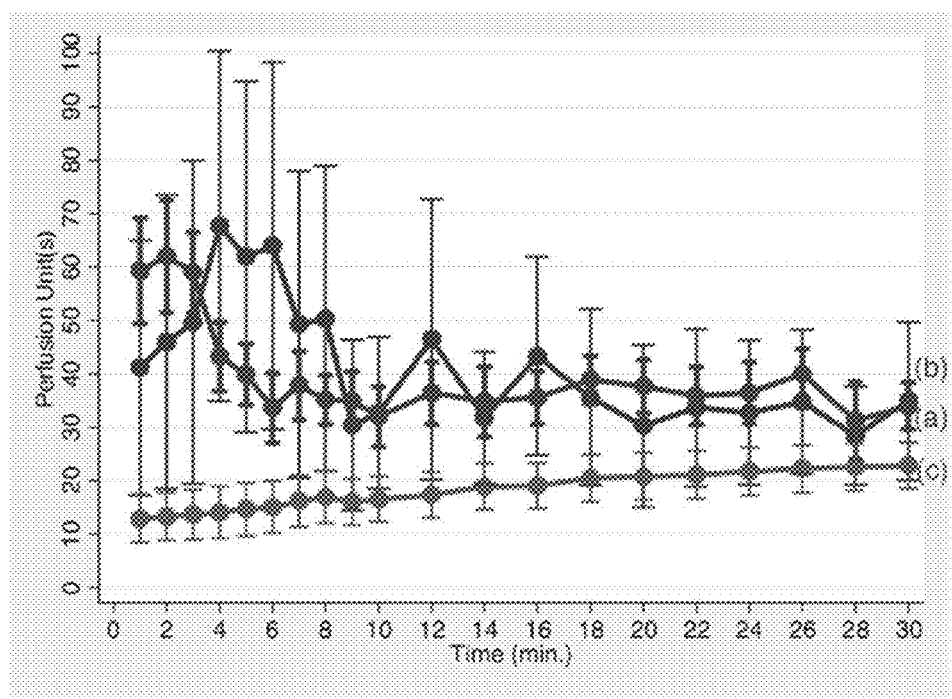
FIG. 4 is a perfusion-time chart for 50% SV patients through with/without prior visible light irradiation.

In an embodiment, the second step of pre-treatment evaluation, the tested skins of the patients receive the visible light irradiation then place on the cold-water packing at 0° C.~4° C. for 10 minutes. After cooling the affected area, the blood flow was recorded by the Doppler Flowmeter. FIG. 3b showed that blood flow patterns of 50% SV patients become progressively stable after irradiated by visible light. In the FIG. 4 shows the other 50% SV patients should not response to visible light irradiation. Thus the results can sever as a standard to determine treating time of patients by visible-light in clinical therapy.

Figure 5:
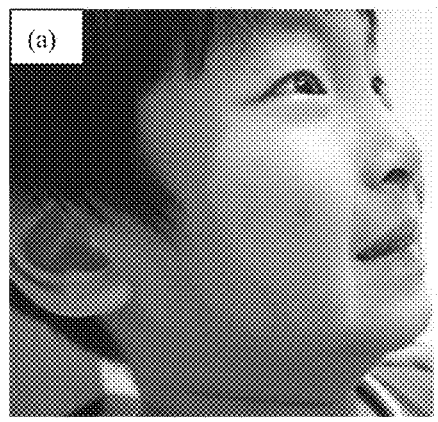
FIG. 5 shows a patient with segmental vitiligo over right face prior to visible light therapy (FIG. 5a). Three months after regular therapy (FIG. 5b). Nine months after regular therapy (FIG. 5c).
Figure 5:
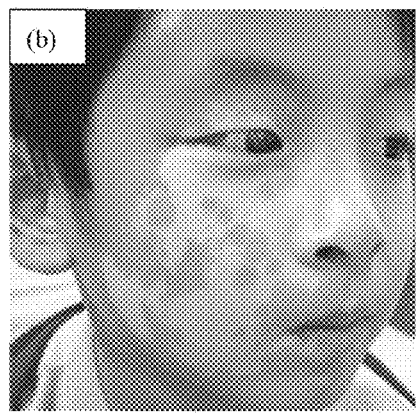
Figure 5:
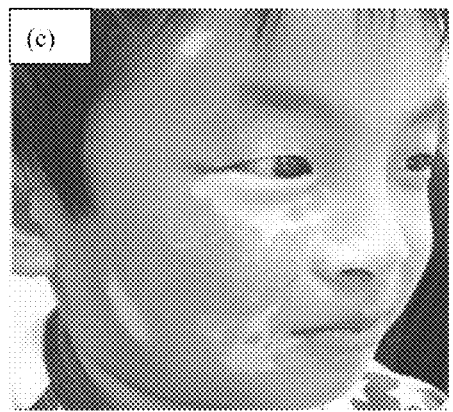

In an embodiment, the third step was to evaluate the time for visible-light treatment on SV patients. Patients were treated with a continuous red visible-light with a red light wavelength of 633±5 nm three times per week for three months. The irradiating flux for each affected area was 3.0 J/cm² every time, and the power output was measured with a power meter (POW-105, Lasotronic). FIG. 5 shows a patient with segmental vitiligo over right face prior to visible light therapy (FIG. 5a). Three months after regular therapy (FIG. 5b). Nine months after regular therapy (FIG. 5c).

TABLE 1

Clinical information of 14 segmental vitiligo patients recruited in the present invention.

| Gender/Age | Sickness Duration | Anatomic Location | Poliosis | Maximum Diameter (cm) |
|---|---|---|---|---|
| Female/31 | 1 yr | face | (+) | 2 |
| Male/63 | 1 yr | face | (−) | 1.5 |
| Female/27 | 1 yr | face | (−) | 2 |
| Male/5 | 1 yr | leg | (−) | 1.5 |
| Male/10 | 5 yr | face | (−) | 1 |
| Female/19 | 7 yr | face | (−) | 2 |
| Male/6 | 2 yr | face | (+) | 4 |
| Female/11 | 6 yr | face | (+) | 4.5 |
| Female/31 | 1 yr | face | (−) | 1 |
| Female/11 | 1 yr | neck | (−) | 2 |
| Female/30 | 1 yr | face | (−) | 1 |
| Female/9 | 2 yr | face | (−) | 1.5 |
| Male/39 | 3 yr | face | (−) | 2 |
| Male/8 | 1 yr | face | (−) | 2.5 |

What is claimed is:

1. A device for evaluating visible-light therapy effect on Segmental Vitiligo (SV) treatment, the device comprising:
   a laser device for irradiating an lesion area with a visible light;
   a cooling device for cooling the affected area with a cool-stress after an irradiation of the visible light; and
   a blood flow detection device for measuring a blood flow of the affected area after the cool-stress, wherein a temperature of the cooling device during the cool-stress is from 0° C. to 4° C.

2. The device as claimed in claim 1, wherein the laser device emits the visible light of red visible light with a wavelength of 633±5 nm.

3. The device as claimed in claim 1, wherein the blood flow detection device is Laser Doppler flowmeter.

4. An evaluating method for visible-light therapy on Segmental Vitiligo (SV), comprising the following steps of:

evaluating a blood flow of an affected area and a normal skin after a cool-stress;
after irradiating a visible-light, cooling and evaluating the blood flow of the affected area; and
after a visible-light treatment, clinically evaluating to determine treatment time,
wherein a temperature of the affected area during the cool-stress is from 0° C. to 4° C. and a cool-stress time is 10 minutes.

5. The evaluating method as claimed in claim 4, wherein the blood flow of the affected area is determined by Laser Doppler flowmeter.

6. The evaluating method as claimed in claim 4, wherein the visible-light irradiated the affected area is a red visible-light with a wavelength of 633±5 nm.

7. The evaluating method as claimed in claim 4, wherein a frequency of visible-light treatment of the affected area is three times a week, for three months with an irradiating flux for each treatment point of 3.0 J/cm$^2$.

\* \* \* \* \*